United States Patent [19]

Suld et al.

[11] 4,031,150

[45] June 21, 1977

[54] CATALYTIC DIMERIZATION OF NORBORNADIENE TO BINOR-S

[75] Inventors: George Suld, Springfield; Abraham Schneider, Overbrook Hills; Harry K. Myers, Jr., Green Ridge, all of Pa.

[73] Assignee: Suntech, Inc., St. Davids, Pa.

[22] Filed: Nov. 14, 1975

[21] Appl. No.: 631,978

[52] U.S. Cl. .................... 260/666 PY; 149/109.4; 149/109.6; 252/431 P

[51] Int. Cl.² .................. C07C 13/28; C06B 43/00; B01J 31/12

[58] Field of Search .......... 260/666 PY; 149/109.4, 149/109.6

[56] References Cited

UNITED STATES PATENTS

| | | | |
|---|---|---|---|
| 3,326,993 | 6/1967 | Bastian et al. | 260/666 PY |
| 3,329,732 | 7/1967 | Bastian et al. | 260/666 PY |
| 3,377,398 | 4/1968 | Zoche | 260/666 PY |
| 3,440,294 | 4/1969 | Pruett et al. | 260/666 PY |
| 3,676,474 | 7/1972 | Tsai et al. | 260/429 R |
| 3,679,722 | 7/1972 | Tsai et al. | 260/429.7 |
| 3,855,323 | 12/1974 | Lyons | 260/666 PY X |

FOREIGN PATENTS OR APPLICATIONS

| | | | |
|---|---|---|---|
| 1,152,776 | 5/1969 | United Kingdom | 260/666 PY |
| 1,108,379 | 4/1968 | United Kingdom | 260/666 PY |

OTHER PUBLICATIONS

Schrauzer et al., (I), Tetrahedron Letters, vol. of 1970, No. 8, pp. 543–545.
Schrauzer, "Advances in Catalysts and Related Subjects", vol. 18, pp. 373–396, (1968).
Schrauzer et al., (II), J. Am. Chem. Soc., vol. 88, pp. 4890–4894, (1966).

*Primary Examiner*—Floyd D. Higel
*Attorney, Agent, or Firm*—Donald R. Johnson; J. Edward Hess; Anthony Potts, Jr.

[57] ABSTRACT

Binor-S is prepared by the dimerization of norbornadiene (bicyclo[2.2.1]hepta-2,5-diene) at an excellent conversion and an excellent selectivity using an effective amount of a two component catalytic system of tris(triphenylphosphine)rhodium chloride and diethylaluminum chloride or ethylaluminum dichloride or aluminum ethylsesquichloride. The range of mole ratio of norbornadiene to tris(triphenylphosphine)rhodium chloride is between from about 100 to about 1000 and the range of mole ratio of one of the aluminum chlorides to the rhodium chloride is between from about 0.5 to about 100. The reaction rate is rapid. Binor-S can be used as precursor for hydrocarbons having utility for either jet or rocket propulsion.

2 Claims, 1 Drawing Figure

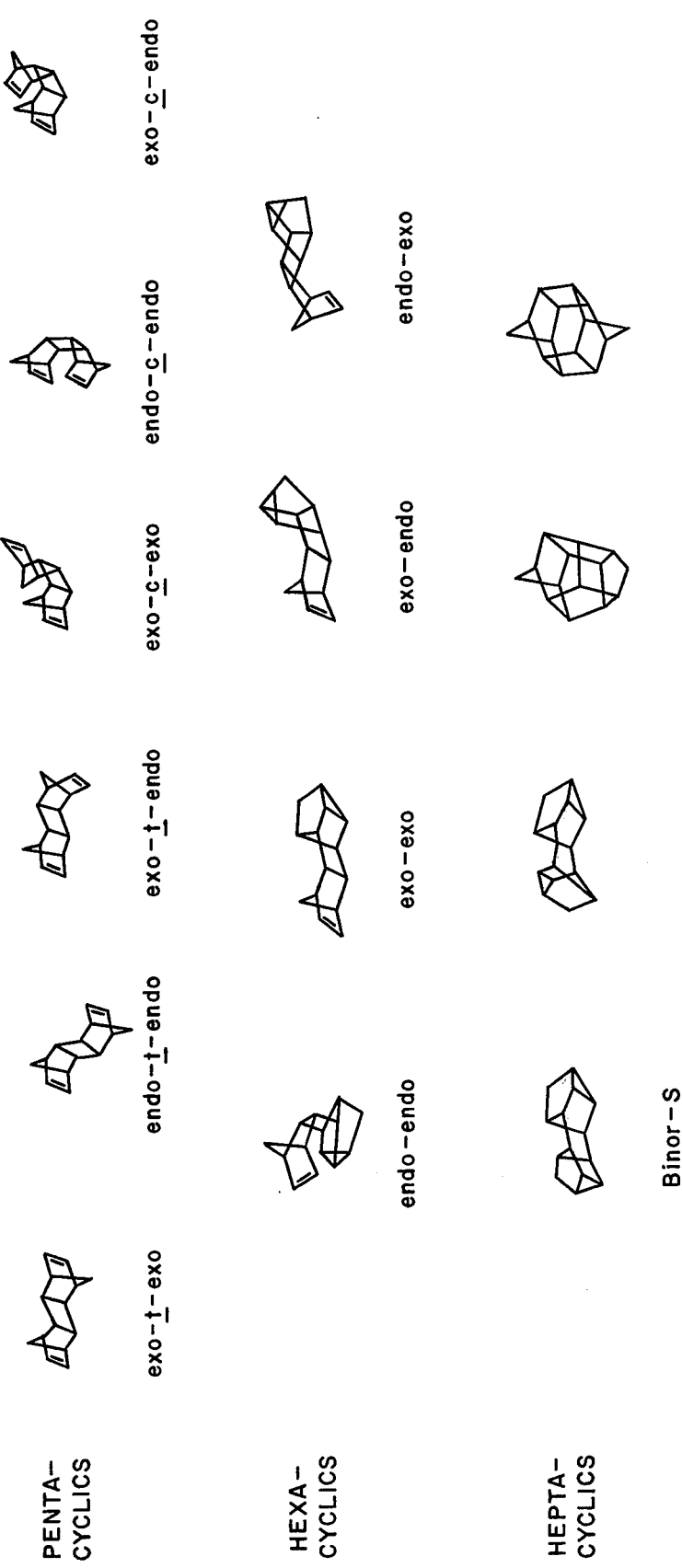
TABLE I
THEORETICALLY POSSIBLE DIMERS OF NORBORNADIENE

CATALYTIC DIMERIZATION OF NORBORNADIENE TO BINOR-S

BACKGROUND OF THE INVENTION

The invention herein described was made in the course of or under a contract thereunder with the United States Air Force Systems Command.

This invention relates to the preparation of Binor-S. More particularly, the invention relates to the preparation of Binor-S from norbornadiene. Still more particularly, the invention relates to the dimerization of norbornadiene to Binor-S.

Binor-S, upon further processing, for example, hydrogenation, can be converted into a component of a high energy fuel which can be used in either jet or rocket propulsion. Jet propulsion includes a jet engine which can be used for a missile plane and others and includes the three basic types, i.e., ramjet, turbo-jet and pulse jet. The term jet generally refers to a device containing its own oxygen or oxidizing agent.

Binor-S is known by the systematic chemical name of endo-cis-endo-heptacyclo $(5.3.1.1^{2,6}.1^{4,12}.1^{9,11}.0^{3,5}.0^{8,10})$-tetradecane. Its melting point is about 65° C.

Preparation of Binor-S is disclosed in an article in the Journal of the American Chemical Society, [88:22] Nov. 5, 1966, pages 4890–4894. The article is titled "π-Complex Multicenter Reactions Promoted by Binuclear Catalysts Systems. "Binor-S", a New Heptacyclotetradicane via Stereospecific Dimerization of Bicycloheptadiene", by G. N. Schrauzer, et al. Disclosed is the dimerization of bycycloheptadiene (also known as norbornadiene) to Binor-S using metal salts of cobalt carbonyl hydrides (e.g., $Zn(Co(CO)_4)_2$). A Lewis acid, such as $AlBr_3$, can be used as a cocatalyst with the transistion metal carbonyl catalyst. Another related article appears in Tetrahedron Letters, No. 8, 1970, pages 543–545 titled "New Catalysts of Stereospecific Norbornadiene Dimerization to "Binor-S", by G. N. Schrauzer et al. This second article discloses the use of $RhCl[P(C_6H_5)_3]_3$ as a catalyst with $BF_3O(C_2H_5)_2$ as a cocatalyst for the dimerization of norbornadiene to Binor-S.

A metal-cobalt carbonyl complex useful as a catalyst in the polymerization of norbornadiene is disclosed in U.S. Pat. No. 3,679,722. Also, U.S. Pat. No. 3,676,474 discloses a multinuclear π-complex having at least two metal cobalt bonds which can be used as a catalyst in the dimerization of norbornadiene.

Norbornadiene is also known as bicyclo(2.2.1) heptadiene-2,5. A method of preparation is disclosed in U.S. Pat. No. 2,875,256 issued Feb. 24, 1959. Norbornadiene will be referred to as NBD hereinafter. NBD can be represented by either one of the following structural formulas:

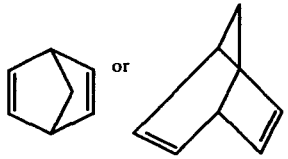

During the dimerization of NBD more than one dimer is possible. G. N. Schrauzer, in his review "On Transition Metal-Catalyzed Reactions of Norbornadiene and the Concept of a Complex Multicenter Processes" in Advances on catalysis 18, 373 (1968) Acad. Press, describes the fourteen theoretically possible dimers of NBD. The possible dimers, grouped according to the number of their carbocyclic rings, are as shown in accompanying Table I. Any and each of the dimers shown in Table I have different physical and chemical properties.

Thus, a specific synthesis problem in the dimerization of NBD, as can be visualized from the number of possible isomers, is to obtain both excellent selectivity and conversion to a desired isomer.

SUMMARY OF THE INVENTION

NBD is rapidly dimerized to Binor-S at both excellent selectivity and conversion. The dimerization requires an effective amount of a two component catalytic system of tris(triphenylphosphine)rhodium chloride and one of the following: diethylaluminum chloride, ethylaluminum dichloride and aluminum ethylsesquichloride. The components are referred to hereinafter as $RhCl[P(C_6H_5)_3]_3$, DEAC, EADC and EASC, respectively. Range of favorable temperatures is specified.

The advantages of the present invention are as follows. The production of Binor-S from NBD is performed with both excellent selectivity and conversion. Furthermore, the reaction rate is rapid. Excellent selectivity and conversion, because the product is almost pure Binor-S, facilitates the conversion of Binor-S to hydrogenated dimer mixtures having a utility as a high energy fuel. Since the product is mostly Binor-S the need to separate it from unreacted feed or other dimers or other compounds is minimized or obviated. Furthermore, the reaction occurs at a relatively low temperature and pressure, both of which reduce the manufacturing cost.

DESCRIPTION

The catalyst dimerization of NBD via present invention can be represented by the following formula reaction.

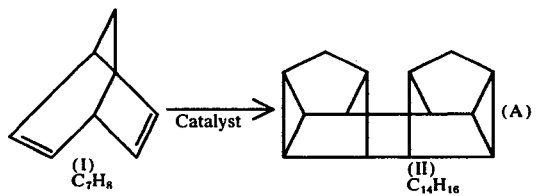

Compound I is NBD while compound II is Binor-S which is also a $C_{14}H_{16}$ heptacyclic dimer of NBD. The structure of II is also often shown as follows:

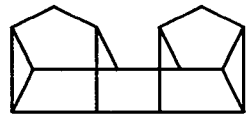

Reaction A may also form small amounts of other dimers as well as heavier compounds. These heavier compounds as well as any unreacted feed and catalyst can be separated from the product by distillation, if necessary. An alternative procedure is that the catalyst can be deactivated by the addition of a hydroxylic solvent, e.g., methanol. This results in formation of two distinct layers with can be separated and then Binor-S can be distilled from other hydrocarbons, if necessary.

The word "product" as used herein refers to compounds fromed as a result of the dimerization reaction A; it does not include unreacted feed.

Generally, the product from reaction A contains a major amount of Binor-S. If the reaction is permitted to run for sufficient time then the product can contain substantial amounts of Binor-S. Based on the runs reported hereinafter the product can contain Binor-S in an excess of 95 mole %, however, at less than optimum conditions the selectively may be lower, e.g., 90%.

The catalytic system favoring the aforementioned dimerization reaction A contains two components. The two are $RhCl[P(C_6M_5)_3]_3$ and DEAC, EADC or EASC. The amount present is an effective amount so that a suitable conversion to Binor-S occurs and the selectivity as to Binor-S is sufficient. Any material which during the dimerization reaction could adversely effect the catalyst system should not be present. For example, the presence of hydroxylic compounds such as water, alcohol or oxygen from air could deactivate the catalyst system.

Selectivity refers to the amount of particular compound formed divided by the amount of all compounds formed. Conversion to the dimer is the amount of total dimer formed divided by the sum of the total dimer plus unreacted feed. From a commercial standpoint economics of an overall process determines the optimal levels for both the selectivity and conversion.

The reaction time required for an economically satisfactory selectivity and/or conversion depend on a number of factors, such as catalyst to NBD ratio, as well as operating conditions. Also the economics depend on capital investment versus conversion per pass and the like. The catalyst to NBD ratios are discussed hereinafter while typical conditions are provided by the Examples.

The amount of $RhCl[P(C_6H_5)_3]_3$ present compared to NBD feed should be sufficient to obtain the desired product. Generally, the mole ratio of NBD to $RhCl[P(C_6H_5)_3]_3$ will range between from about 100 to about 1000 with a more typical range between from about 250 to about 750.

DEAC, EADC or EASC is the second component of the catalyst system with EADC preferred. The amount of the second component can vary substantially but generally it relates to the amount of $RhCl[P(C_6H_5)_3]_3$ used. An effective mole ratio range of DEAC, EADC or EASC or $RhCl[P(C_6H_5)_3]_3$ can be between from about 0.5 to about 100 with about 2 to about 50 preferred and about 5 to about 20 more preferred. Excess DEAC, EADC, or EASC also serves as a scavenger for any water and/or oxygen in the system. Generally, however, when DEAC or EADC or EASC is used it is advantageous to conduct the reaction under substantially anhydrous conditions and under an inert gas blanket.

A suitable solvent can be used in the dimerization reaction. Since the reaction is exothermic a solvent may serve as a heat sink. It can also assist in solubilizing the reaction components, that is the feed and the components of the catalyst and thereby provide for a homogeneous reaction medium. As stated previously, the solvent should not adversely react with the feed, products or catalyst. Also, presence of a solvent facilitates the handling of the reaction mixture. Classes of suitable solvents include aromatic hydrocarbons, cycloparaffins, halogenated aromatics, halogenated paraffins and halogenated cycloparaffins. Specific examples include benzene, toluene, xylenes, cyclohexane, chlorobenzene, bromobenzene, chlorinated cyclohexane and the like. As to the amount of solvent used, excessive amounts decrease the reaction rate, and thus adversely affect the economics for a commercial operation.

Selective dimerization of NBD occurs in the liquid phase therefore it is not desirable to have the reaction temperature largely exceed the boiling points of the NBD and/or solvent. Conversely, if the temperature is too low the reaction rate would be too low to be economically feasible. An operable temperature range is between from about 25° to about 150° C with about 50° to about 100° C a preferred range. The operating pressure can vary substantially, however, it can range from about atmospheric up to about 2000 psi with 1000 psi a preferred upper value. Process economics favor lower operating pressure, however, a moderately elevated reaction pressure may be desirable to keep gaseous reaction components in solution.

The selective NBD dimerization of the present invention can be carried out in either a batch or a continuous process.

To further illustrate the invention, the following examples are provided.

EXAMPLES

The accompanying Table II summarizes the dimerization runs which were carried out in 50 ml pyrex vessels closed with wired serum caps fitted with an internal immersion thermometer. The procedure was as follows. First the tubes were flushed with argon. Then the materials were added to the tubes in the following order: $RhCl[P(C_6H_5)_3]_3$, solvent, NBD (99% pure) and DEAC or EADC all at room temperature. This sequence was satisfactory and it is believed that other sequences will work equally well. Prior to use the NBD (Aldrich, 99% pure) was percolated through alumina.

The test tubes were heated in an oil bath with temperatures as indicated in Table II. The conversions and selectivities reported in Table II are based on analyses performed by vapor phase chromatography on both packed and capillary columns.

TABLE II

| | | | Dimerization of NBD** | | | |
|---|---|---|---|---|---|---|
| | | | Other Cat. Component | | | |
| Run | Time++ | Amount* of Rh (TPP)₃Cl | Type | Amount* | % Conversion+ | Binor-S Selectivity % |
| 1a | 30 | 0.06 | DEAC | 0.4 | 45.9 | *** |
| b | 120 | 0.06 | DEAC | 0.4 | 55.4 | 96 |

TABLE II-continued

| | | | Dimerization of NBD** | | | |
|---|---|---|---|---|---|---|
| | | Amount* of | Other Cat. Component | | | Binor-S |
| Run | Time++ | Rh (TPP)₃Cl | Type | Amount* | % Conversion+ | Selectivity % |
| 2 | 20 | 0.06 | EADC | 0.5 | 93.5 | 97 | millimoles
*temperature was about 70–80° C, 30 millimoles of NBD and 1 milliliter of solvent (toluene) were used.
***not analyzed
+to the dimer
++minutes In both runs 1b and 2, selectivities were in excess of 95%. Such high selectivities indicate the absence of substantial amounts of any volatile coproducts.

Similar results can be obtained using other solvents, e.g., cycloparaffins, halogenated aromatics, disclosed herein; and at other amounts than those used in runs 1 and 2. Also, similar conversions and selectivities can be obtained using other ratios of NBD to RhCl[P(C₆H₅)₃]₃, e.g., 250 or 750 and/or other ratios of DEAC or EADC to RhCl[P(CH₆H₅)₃]₃, e.g., 2 or 50. also similar results can be obtained using EASC.

It should be noted that the feed to the foregoing reaction A consists essentially of NBD. Thus, for example, additional reactive monoolefinic and diolefinic hydrocarbons should be generally excluded.

The invention claimed is:

1. Process for the catalytic dimerization of norbornadiene comprising:

a. reacting a feed consisting essentially of norbornadiene in the presence of an effective amount of a two-component catalytic system of tris(triphenylphosphine) rhodium chloride and one of the following: diethylaluminum chloride, ethylaluminum dichloride and aluminum ethylsesquichloride; and wherein the range of mole ratio of norbonadiene to tris(triphenylphosphine) rhodium chloride is between from about 100 to about 1000; and wherein the range of mole ration of diethylaluminum chloride or ethylaluminum dichloride or aluminum ethylsesquichloride to tris(triphenylphosphine) rhodium chloride is between from about 0.5 to about 100; and wherein the reacting occurs in the presence of a suitable solvent selected from the group consisting of aromatic hydrocarbons, cycloparaffins, halogenated aromatics, halogenated paraffins and halogenated cycloparaffins; and thereby provides a homogeneous reaction medium;

b. the reacting occurring within a temperature range between from about 25° to about 150° C; and whereby the major product is Binor-S.

2. Process according to claim 1 wherein the amount of Binor-S is substantial.

* * * * *